United States Patent [19]

Künstle et al.

[11] 4,207,259

[45] Jun. 10, 1980

[54] PROCESS FOR THE MANUFACTURE OF α-CHLORACETOACETAMIDES

[75] Inventors: Gerhard Künstle, Raitenhaslach; Herbert Jung, Burghausen, both of Fed. Rep. of Germany

[73] Assignee: Wacker-Chemie GmbH, Munich, Fed. Rep. of Germany

[21] Appl. No.: 42,700

[22] Filed: May 25, 1979

[30] Foreign Application Priority Data

Jun. 1, 1978 [DE] Fed. Rep. of Germany ....... 2824046

[51] Int. Cl.² .......................................... C07C 103/30
[52] U.S. Cl. ......................... 260/561 K; 260/561 HL
[58] Field of Search ..................... 260/561 K, 561 HL

[56] References Cited

U.S. PATENT DOCUMENTS

| | | | |
|---|---|---|---|
| 3,284,500 | 11/1966 | Tieman | 260/561 K |
| 3,358,023 | 12/1967 | Birtwistle | 260/561 HL |
| 3,449,421 | 6/1969 | Pearson | 260/561 K |
| 3,483,252 | 12/1969 | Beriget | 260/561 K |
| 3,852,351 | 12/1974 | Scharpf | 260/561 K |
| 3,917,694 | 11/1975 | Reinink | 260/561 K |

*Primary Examiner*—Arthur P. Demers
*Attorney, Agent, or Firm*—Allison C. Collard; Thomas M. Galgano

[57] ABSTRACT

According to the invention, α-chloracetoacetamides, which is to be understood as including both α-chloro-N-monoalkylacetoacetamides and α-chloro-N,N-dialkylacetoacetamides, the alkyl radicals of which contain 1 to 3 carbon atoms, are produced by reacting the corresponding acetoacetamides with chlorine in aqueous solution at temperatures in the range of from $-1°$ C. to $-25°$ C. At a conversion of at least 95%, a selectivity of at least 97% and a yield of at least 95% of the theoretical yield, calculated on reacted acetoacetamide, are obtained.

6 Claims, No Drawings

PROCESS FOR THE MANUFACTURE OF α-CHLORACETOACETAMIDES

The present invention relates to a process for the manufacture of α-chloracetoacetamides by chlorination of acetoacetamides with stoichiometric amounts of chlorine at temperatures below 0° C. in the presence of aqueous solvents.

α-Chloracetoacetamides are valuable intermediates for the manufacture of insecticides based on phosphoric acid esters, especially dialkyl phosphates of N-monoalkyl-3-hydroxycrotonic acid amides and N,N-dialkyl-3-hydroxycrotonic acid amides (cf. U.S. Pat. No. 2,802,855).

α-Chloracetoacetamides have hitherto been manufactured by chlorinating corresponding acetoacetamides. In this process, substantial amounts of α,α-dichloracetoacetamides are formed as by-products, and their separation is practically impossible, owing to their similar physical properties. Consequently, several processes have already become known, which give practically pure α-chloracetoacetamides by means of a subsequent selective dehalogenation of the α,α-dichloracetoacetamides. However, these processes necessitate additional steps, and, therefore, involve uneconomically high costs of production.

According to the process described in German Pat. No. 1,493,022 (which corresponds to U.S. Pat. No. 3,449,421,) which is limited to the manufacture of α-chloro-N,N-dialkylacetoacetamides, the chlorination of the N,N-dialkylacetoacetamides can be carried out with hypochlorous acid, N-chlorourea and/or tert.-butyl hypochlorite at temperatures of 0° C. to 80° C. Water is recommended here as a suitable solvent, especially when the chlorinating agent used is hypochlorous acid, which can be produced in situ by reacting chlorine with water. Since the reaction progresses too slowly in the lower temperature range, the process is advantageously carried out at room temperature and above, and the selectivity is improved by the simultaneous use of urea. As can be seen from Example 2, under these conditions, 96.4% of α-chloro-N,N-dimethylacetoacetamide, in addition to 0.6% of α,α-dichloro-N,N-dimethylacetoacetamide and 1.1% of N,N-dimethylacetoacetamide (unreacted starting material,) are obtained, corresponding to a conversion of 92.6%.

The transfer of this process to the manufacture of α-chloro-N-monoalkylacetoacetamides, such as α-chloro-N-methylacetoacetamide, was, however, not possible without the formation of large quantities of the corresponding α,α-dichloro-N-methylacetoacetamide. German Pat. No. 1,618,207 (which corresponds to U.S. Pat. No. 3,483,252,) therefore describes a process in which N-monoalkylacetoacetamides are chlorinated at temperatures below 0° C., that is, in the range of from −8° C. to −25° C., in the presence of water and urea, and in which in addition, the presence of an alcohol is necessary. As can be seen from Example 1, under these conditions, 90% of α-chloro-N-methylacetoacetamide, in addition to 5% of α,α-dichloro-N-methylacetoacetamide and 1.6% of unreacted starting material, are obtained.

This process, too, could, however, not be satisfactorily used on an industrial scale, since the quantity of α,α-dichloro compounds formed as undesired by-products, is still too large, and the large amounts of urea required (0.5 mole per mole of chlorine) are extremely uneconomical.

According to the process described in German Offenlegungsschrift No. 2,049,045 (which corresponds to Dutch Application No. 70 14 636,) it should, however, be possible to chlorinate both N-monoalkyl-acetoacetamides and N,N-dialkyl-acetoacetamides at temperatures below 0° C. without the addition of urea, if an alkanol having 1 to 6 carbons atoms is used as a solvent that optionally contains 5% to 40% water, preferably, approximately, 15% to 20% water. The selectivity of this process with respect to the formation of the desired α-monochloro derivatives is said to be increased in comparison with the hitherto known processes, since only approximately 5% of the α,α-dichloro derivatives are formed, which, after removing the alkanol, may optionally be selectively dehalogenated in known manner by treatment with a reducing agent. As can be seen from the examples, which are concerned exclusively with the chlorination of N-monomethylacetoacetamide, the best results regarding conversion and selectivity were obtained by using ethanol containing 7.4% water, as a solvent. However, an increase in the water content to 50% or more, even to 75%, under otherwise identical conditions, resulted in a marked reduction in the conversion and the selectivity. This German Offenlegungsschrift No. 2,049,045 therefore teaches that the chlorination of acetoacetamides, especially N-monomethylacetoacetamides, can be carried out at temperatures below −15° C., to form the corresponding α-monochloro derivatives, with a conversion of more than 95% and a selectivity of the same order of magnitude, in acceptable reaction times, e.g., within approximately two hours, only in dilution with an alkanol of which the water content must not exceed 20%. Any variation in these reaction conditions, especially an increase in the water content in the prescribed solvent, results in a reduction in the conversion and/or the selectivity, and it is expressly mentioned that as the water content increases, so does the reaction time. In practice, therefore, the use of this process is extremely limited. Furthermore, additional steps are required for the removal of the alkanol by distillation, before the reaction product can be worked up in known manner.

These narrow limits were clearly recognized by the applicant himself, as can be seen from the comments concerning the state of the art in U.S. Pat. No. 3,917,694, in which it is mentioned that in this process, conversion and selectivity in many cases have the tendency to decrease, when the reaction is carried out on a large scale. In this U.S. patent, therefore, the process for chlorinating N-alkylacetoacetamides or N,N-dialkylacetoacetamides at temperatures below 0° C. and with the use of alkanol as solvent, is modified by limiting the speed of introduction of the chlorine at the beginning, and progressively increasing it as the reaction proceeds. By this means, a constant and high conversion and selectivity is said to be achieved. As can be seen from the Examples, however, in the case of chlorination of N-monomethylacetoacetamide, good results are achieved only if urea is simultaneously used in quantities of up to 1 mole per mole of N-monomethylacetoacetamide, and so the use of the name "chlorinating catalyst" for the urea is no longer jusfified, owing to the large amount required.

These known processes show that in the chlorination of acetoacetamides with chlorine, the selectivity with respect to the desired formation of the corresponding monochloro compounds, can be positively influenced by lowering the reaction temperature, by the choice of solvent and/or by slowing down the speed of introduction of the chlorine. Achieving high selectivity, however, is in practice reasonable only when it must not be achieved at the cost of an incomplete reaction. High selectivity with simultaneously high conversion, however, can be achieved in the hitherto known processes, only by means of complicated steps, especially in the case of chlorination of N-monoalkylacetoacetamides, which, with regard to the undesired formation of α,α-dichloro compounds, react more sensitively to a varying degree than the corresponding N,N-dialkylacetoacetamides.

It is therefore the object of the instant invention to provide a simplified process for the manufacture of α-chloracetoacetamides of the general formula $$CH_3COCH(Cl)CONR_1R_2$$

in which
$R_1$ represents alkyl radicals having 1 to 3 carbon atoms; and
$R_2$ represents hydrogen or alkyl radicals having 1 to 3 carbon atoms,
by reacting acetoacetamides of the general formula $$CH_3COCH_2CONR_1R_2$$

in which $R_1$ and $R_2$ have the meaning given above, with chlorine in stoichiometric amounts, in the presence of water-containing solvents at temperatures below 0° C., which, with a conversion of at least 95%, guarantees a high selectivity of at least 97%, without requiring additional complicated steps, such as connecting an additional distillation stage for removing the solvent, regulating the speed of the introduction of the chlorine, let alone using uneconomically large quantities of urea.

According to the instant invention, this problem is solved by exclusively using water as a solvent, and carrying out the reaction in the liquid phase.

In the process according to the instant invention, either N-monoalkylacetoacetamides or N,N-dialkylacetoacetamides can be used as starting materials, either in pure form or in the form of concentrated aqueous solutions.

Examples of N-monoalkylacetoacetamides are N-methyl-, N-ethyl-, N-isopropyl- and N-n-propylacetoacetamide. Examples of N,N-dialkylacetoacetamides are N-N-dimethyl-, N-N-diethyl-, N-N-di-n-propyl- and N,N-diisopropyl-acetoacetamide, wherein N-methyl-, N-ethyl-, N,N-dimethyl- and N,N-diethylacetoacetamide, are preferred.

The reactants, that is, acetoacetamides and chlorine, are advantageously used in a molar ratio of approximately 1:1, but especially in the case of N-monoalkylacetoacetamide, a molar ratio within the range of 1:0.8 to 0.95, preferably, to 0.90, has proved advantageous. A chlorine excess is to be avoided, because this adversely affects the selectivity.

The process according to the instant invention, can be carried out at temperatures within the range of from −1° C. to −25° C., discontinuously or continuously. For the manufacture of α-chloro-N-monoalkylacetoacetamides, temperatures within the range of from −18° C. to −23° C., have proved especially advantageous, whereas for the manufacture of α-chloro-N,N-dialkylacetoacetamides, temperatures within the range of from −1° C. to −10° C. are preferred for reasons of economy and processing techniques.

The decisive feature in carrying out the process of the instant invention is that water is used exclusively as the reaction medium. To ensure that the reaction is carried out in the liquid phase even in the lower temperature range, an inorganic salt can be added to the starting mixture in the amount necessary to reduce the freezing point to the reaction temperature. Chlorides of sodium, calcium and/or magnesium have proved particularly suitable for this purpose. It is also possible to use other inorganic salts that are inert with respect to the reactants, such as $KH_2PO_4$ or $K_2HPO_4$. In addition, good mixing of the reactants can be achieved by doing so by mechanical means.

The quantity of water required for carrying out the process according to the instant invention, can be varied within a wide range, depending on the solubility of the reactants and of the inorganic salt additives, which are optionally present and inert to the reaction. At least 0.5 part by weight of water is necessary, however, per part by weight of acetoacetamide. It is, however, also possible to use up to 15 parts by weight of water per part by weight of acetoacetamide. The upper limit is especially based on considerations concerning the processing technology, since, as is known, a small reaction volume is advantageous in order to achieve a good space/time yield. Preferably, 0.7 to 7 parts by weight of water are used per part by weight of acetoacetamide.

When chlorination is complete, the reaction mixture is worked up in a known manner, e.g., the reaction products are separated from the aqueous phase by extraction with a water-immiscible organic solvent, such as benzene, toluene chloroform or dichloromethane. Neutralization of the organic phase is not necessary here: Instead, this can be further processed without additional steps, e.g., after the extraction agent and the hydrogen chloride formed in the chlorination process have been distilled off, the desired α-chloracetoacetamide is left as residue.

Neutralization of the aqueous phase, on the other hand, is necessary only if the process is carried out continuously, and the aqueous phase is again used as the reaction medium for the chlorination, e.g., it is recycled, since hydrogen chloride dissolved therein, impairs the selectivity when chlorination is carried out again. In this case, it is advantageous for the neutralization to be carried out with aqueous sodium hydroxide solution, since this produces the quantity of sodium chloride necessary to reduce the freezing point of the reaction medium, rendering possible further simplification of the process.

According to the process of the present invention, α-chloromonoalkylacetoacetamides can be produced with a selectivity of up to 99.5%, with a conversion of more than 95.5%, and in a yield of up to 95.5% of the theoretical yield, calculated on reacted monoalkylacetoacetamide, and α-chlorodialkylacetoacetamides can be produced with a selectivity of up to 100%, with a conversion likewise of up to 100%, and in a yield of up to 99.5% of the theoretical yield, calculated on reacted N,N-dialkylacetoacetamide, which was not possible according to the hitherto known processes. This result must be regarded as surprising, especially in view of the fact that increasing the quantity of water in an alkanol-containing reaction mediium, results in a reduction in the selectivity and conversion.

The instant invention will now be more fully described in a number of Examples, which, however, are given only by way of illustration and not of limitation.

EXAMPLE 1

The apparatus used for chlorination consisted of an enamelled reaction agitator with an inlet tube, a cooling jacket, and a bottom outlet, to which was attached an inspection glass for the layer separation.

The reaction agitator was charged, in the given order, with
773 parts of water
227 parts by weight of industrially pure NaCl, and
115.7 parts by weight of 99.5% N-methyl-acetoacetamide (MMAA).

While stirring at $-19°$ C. to $-22°$ C., a total of 56.7 parts by weight of gaseous chlorine were introduced under the surface of this mixture in the course of one hour.

The resulting reaction mixture was then exhaustively extracted with benzene at room temperature, the benzene phase was worked up by distillation, and the aqueous phase was neutralized with 50% sodium hydroxide solution at room temperature. In the distillative working up of the benzene phase, the benzene was practically completely removed by simply being driven off in vacuo (approximately 560 mbar, only towards the end of the process was the vacuum increased to 6.5 mbar,) wherein the sump temperature did not exceed 85° C. The resulting residue was a melt, solidifying at 78° C. and having the following composition:
97.4% by weight of N-methyl-α-chloraceto-acetamide (MMCAA),
2.0% by weight of N-methylacetoacetamide (MMAA),
0.6% by weight of N-methyl-α,α-dichloracetoacetamide (MMDCAA).

The neutral, NaCl-containing, aqueous phase with a residual MMAA content of 21.6 parts by weight, was introduced into the reaction agitator again, with 50 parts of water and 94.0 parts by weight of 99.5% N-methylacetoacetamide being added, and chlorination and working up were carried out as described above.

Altogether, the aqueous phase was subjected to chlorination five times. A total of 492 parts by weight of N-methylacetoacetamide (MMAA) of 99.5% strength, and 283.5 parts by weight of chlorine were used, and altogether 588.6 parts by weight of 97.4% N-methyl-α-chloracetoacetamide (MMCAA) were obtained, that is, 96.8% of the theoretical yield, calculated on reacted MMAA.

11.8 parts by weight of MMAA were still contained in the MMCAA. The MMAA-conversion was 95.6% and the selectivity, 99.5%. Practically the same results were obtained when, instead of NaCl, 203 parts by weight of CaCl$_2$ or 163 parts by weight of MgCl$_2$ were used. Also, the same result is obtained by using dichloromethane as an extracting agent instead of benzene.

EXAMPLES 2 and 3

The process according to Example 1 was repeated, but with a different molar ratio of chlorine to MMAA. The results are compiled in the following Table I:

TABLE I

| Example No. | Molar ratio chlorine:MMAA | Composition of the product (% by weight) | | |
|---|---|---|---|---|
| | | MMCAA | MMAA | MMDCAA |
| 1 | 0.8:1 | 97.4 | 2.0 | 0.6 |

TABLE I-continued

| Example No. | Molar ratio chlorine:MMAA | Composition of the product (% by weight) | | |
|---|---|---|---|---|
| | | MMCAA | MMAA | MMDCAA |
| 2 | 0.9:1 | 96.5 | 2.5 | 0.9 |
| 3 | 0.95:1 | 95.5 | 2.0 | 1.5 |

EXAMPLE 4

The process according to Example 1 was repeated, except that, instead of 99.5% N-methylacetoacetamide, an aqueous 68.7% solution was used, which had been produced by reacting diketene with aqueous 40% methylamine.

A total of 712 parts by weight of a 68.7% N-methylacetoacetamide solution (MMAA) was used, and 580.5 parts by weight of N-methyl-α-chloracetoacetamide (MMCAA) of the same composition as that described in Example 1 were obtained, that is, 95.5% of the theoretical yield calculated on reacted MMAA.

EXAMPLE 5

The process according to Example 1 was repeated, except that, once chlorination was complete, the reaction mixture was cooled and the suspension filtered. The resulting solid was extracted with benzene, and the extract further treated as described in Example 1.

The resulting residue was 309.4 parts by weight of a melt solidifying at 80° C., and this was 99.5% pure N-methyl-2-chloracetoacetamide (MMCAA,) that is, 52% of the theoretical yield, calculated on reacted MMAA. The remaining mother liquor was worked up, as described in Example 1; and from this, a further 260 parts by weight of MMCAA of 100% strength were obtained.

EXAMPLE 6

The apparatus described in Example 1 was used. The reaction vessel was charged, in the given order, while stirring, with
90 parts of water, and
129.7 parts by weight of 99.5% N,N-dimethylacetoacetamide (DMAA)
and cooled to $-5°$ C. to $-3°$ C. While stirring further, a total of 71 parts by weight of gaseous chlorine was introduced under the surface of the mixture, within this temperature range over the course of one hour.

The reaction mixture was then exhaustively extracted with chloroform at room temperature, the organic phase was worked up by distillation, and the aqueous phase was discarded. In the working up by distillation of the chloroform phase, the chloroform was practically completely removed simply by driving off in vacuo (initially, 550 mbar, towards the end of the process, 6.5 mbar,) wherein the sump temperature did not exceed 80° C.

The residue was 163.1 parts by weight of N,N-dimethyl-2-chloracetoacetamide (DMCAA) of the following composition:
99.5% by weight of N,N-dimethyl-α-chloracetoacetamide (DMCAA),
0.1% by weight of N,N-dimethylacetoacetamide (DMAA),
0.4% by weight of N,N-dimethyl-α,α-dichloracetoacetamide (DMDCAA).

The boiling point of the resulting DMCAA was 110° C. at 0.13 mbar. At a conversion of practically 100%, the selectivity was practically 100% and the yield, 99.2% of the theoretical yield.

EXAMPLES 7 to 10

The process according to Example 6 was repeated, but observing the conditions listed in the following Table II.

TABLE II

| Example No. | Reaction temp. °C. | Molar ratio of DMAA to Chlorine | Reaction time (hours) | Part of water per part by wt. of DMAA | Extraction agent | Composition of the product | | |
|---|---|---|---|---|---|---|---|---|
| | | | | | | DMCAA[1] | DMAA | DMDCAA[2] |
| 7 | −20 | 1:0.9 | 1.5 | 0.70 | Benzene | 98.5 | 1.5 | 0 |
| 8 | −10 | 1:0.9 | 1.5 | 0.70 | chloroform | 98.5 | 1.4 | 0.05 |
| 9 | −5 | 1:0.9 | 1.5 | 0.70 | Benzene | 98.5 | 1.0 | 0.1 |
| 10* | ±0 | 1:1 | 1.5 | 0 | chloroform | 69.5 | 0.7 | 29.8 |

[1]DMCAA = N,N-dimethyl-α-chloracetoacetamide
[2]DMDCAA = N,N-dimethyl-α,α-dichloracetoacetamide
*For comparison, without solvent It will be obvious to those skilled in the art that other changes and variations can be made in carrying out the present invention, without departing from the spirit and scope thereof, as defined in the appended claims.

What is claimed is:

1. A process for the manufacture of α-chloracetoacetamides of the general formula $$CH_3COCH(Cl)CONR_1R_2$$

in which
   $R_1$ represents alkyl radicals having 1 to 3 carbon atoms, and
   $R_2$ represents hydrogen or alkyl radicals having 1 to 3 carbon atoms,
by reacting acetoacetamides of the general formula $$CH_3COCH_2CONR_1R_2$$

in which $R_1$ and $R_2$ have the meanings given above, with chlorine in stoichiometric amounts, in the presence of aqueous solvents, at temperatures below 0° C., characterized in that water is exclusively used as the solvent, and the reaction is carried out in the liquid phase.

2. The process according to claim 1, wherein in the reaction, acetoacetamides and chlorine are used in the molar ratio of 1:0.8 to 0.9.

3. The process according to claim 1, wherein the reaction is carried out at a temperature within the range of from −1° C. to −25° C.

4. The process according to claim 1, wherein an inorganic salt is added to the starting mixture in the amount required to reduce the freezing point to the reaction temperature.

5. The process according to claim 4, wherein chlorides of sodium, calcium or magnesium are used as inorganic salts.

6. The process according to claim 1, wherein 0.7 to 7 parts by weight of water are used per part by weight of acetoacetamide.

* * * * *